United States Patent [19]

Wolf

[11] 4,216,147

[45] Aug. 5, 1980

[54] N-METHYL-N-(SUBSTITUTED CARBONYLAMINOTHIO)CARBAMATES

[75] Inventor: Anthony D. Wolf, Newark, Del.

[73] Assignee: E. I. Du Pont de Nemours and Company, Wilmington, Del.

[21] Appl. No.: 957,231

[22] Filed: Nov. 2, 1978

[51] Int. Cl.$^2$ .............................................. C09B 29/14
[52] U.S. Cl. .................................. 260/207; 260/194; 260/195; 260/196; 260/197; 260/200; 260/207.1; 424/226
[58] Field of Search ..................... 260/207.1, 207, 194, 260/195, 196, 197, 200; 424/226

[56] References Cited

U.S. PATENT DOCUMENTS

| | | | |
|---|---|---|---|
| 2,300,676 | 11/1942 | Kharasch et al. | 260/207.1 X |
| 3,793,456 | 2/1974 | Wright et al. | 424/226 |
| 3,987,108 | 10/1976 | Karrer | 260/207.1 X |
| 4,110,444 | 8/1978 | Wight et al. | 260/207.1 X |

FOREIGN PATENT DOCUMENTS 2654246  6/1977  Fed. Rep. of Germany ........... 260/327

*Primary Examiner*—Helen M. S. Sneed

[57] ABSTRACT

N-methyl-N-(substituted carbonylaminothio)carbamates exhibit high insecticidal and/or nematicidal activity with reduced phytotoxicity.

10 Claims, No Drawings

N-METHYL-N-(SUBSTITUTED CARBONYLAMINOTHIO)CARBAMATES

BACKGROUND OF THE INVENTION

This invention relates to insecticidal carbamates and, more particularly, to N-methyl-N-(substituted carbonylaminothio) carbamates which demonstrate high insecticidal activity.

Belgian Pat. No. 848,913, granted May 31, 1977, relates to pesticidal unsymmetrical bis-carbamoyl sulfide compounds of the general formula:

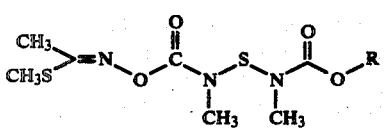

where
R can be alkynyl, alkenyl, phenyl, substituted phenyl or naphthyl.

SUMMARY OF THE INVENTION

This invention relates to compounds of Formula I, to insecticidal and/or nematicidal compositions containing them and to the method of using said compounds as insecticides and/or nematicides:

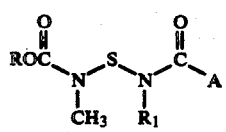

wherein

R is

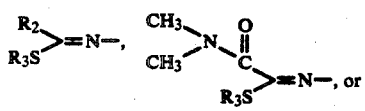

where
$R_1$ and $R_3$ are $C_1$–$C_3$ alkyl;
$R_2$ is $C_1$–$C_3$ alkyl or $CH_3OCH_2$; and

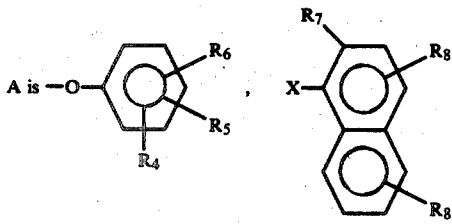

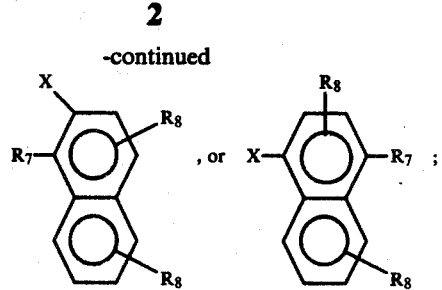

where
$R_4$ and $R_5$ are H, $C_1$–$C_4$ alkyl, halogen, —$CO_2H$ or —$SO_3Na$;
$R_6$ is o or p —N=N—B;
$R_7$ is —N=N—B;
$R_8$ is H or $SO_3Na$;

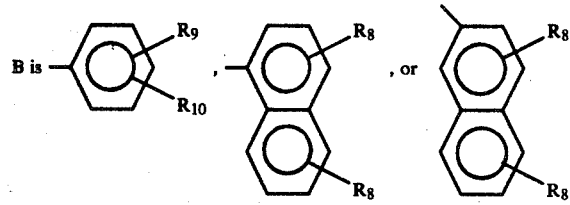

where
$R_9$ and $R_{10}$ are H, $C_1$–$C_4$ alkyl, halogen, —$CO_2H$, —$SO_3Na$, $NO_2$, or $C_1$–$C_3$ alkoxy; and
X is NH or O.

DETAILED DESCRIPTION OF THE INVENTION

Preferred compounds

The following groups of compounds of Formula I are preferred for their high insecticidal or nematicidal activity:

(1) Those compounds wherein X is oxygen;
(2) Those compounds wherein R is

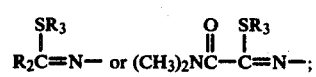

(3) Those compounds wherein

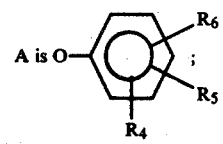

(4) Those compounds wherein

-continued

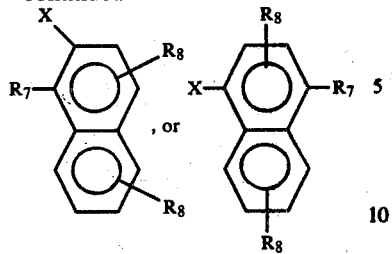
, or

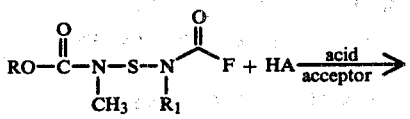

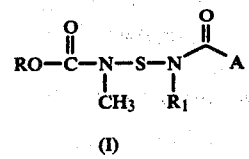

(5) Those compounds wherein

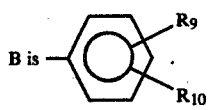

More preferred for their higher insecticidal or nematicidal activity are the following groups of compounds of Formula I:
(1) Those compounds wherein:

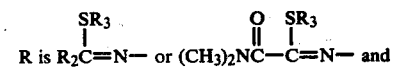

R is $R_2C=N-$ or $(CH_3)_2NC-C=N-$ and

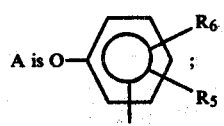

(2) Those compounds of group (1) wherein

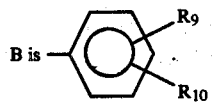

Most preferred for their ease of synthesis, cost and/or higher insecticidal or nematicidal activity are those compounds of Formula I wherein

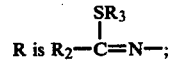

R is $R_2-C=N-$;

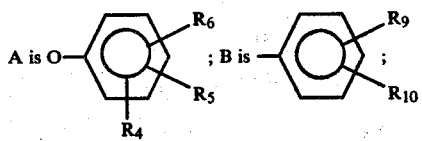

$R_2$ is $C_1-C_2$ alkyl; and
$R_3$ is methyl.

Specifically preferred for its favorable cost and its insecticidal activity is methyl N-[N-[N-[4-(2,6-diethylphenylazo)-2-methylphenoxycarbonyl]-N-methylaminothio]-N-methylaminocarbonyloxy]ethanimidothioate.

Preparation

Compounds of Formula I can be prepared as shown in Equation I, wherein R, $R_1$ and A are as previously defined, by reacting a carbamoyl fluoride (1) with the appropriate phenol or naphthol (2).

The reaction can be carried out in an inert organic solvent, such as benzene, toluene, the xylenes, methylene chloride, chloroform, ethylene dichloride, acetone, methyl ethyl ketone, dioxane, tetrahydrofuran, acetonitrile, or dimethylformamide. Mixtures of these solvents may be used. The reaction can be carried out at temperatures between 0° and 150° C., preferably between 20° and 100° C. Pressure is not critical for the reaction procedure since pressures above and below atmospheric are suitable. For convenience, atmospheric pressure is preferred.

The acid acceptor used in Equation I can be a tertiary organic amine, such as trimethylamine, triethylamine, N,N-dimethylaniline, or pyridine, or an inorganic base, such as the alkali metal and alkaline earth metal hydroxides, carbonates, bicarbonates, and alkoxides, such as sodium methoxide or potassium tert-butoxide.

The compounds of Formula I obtained by the reaction described in Equation I can be purified by methods known to those skilled in the art, such as recrystallization, column chromatography or other suitable procedure.

Carbamyl fluorides of Formula I can be prepared by reacting hydrogen fluoride with an appropriate alkyl isocyanate to form an alkylaminocarbonylfluoride compound which may then be reacted with sulfur dichloride to produce the desired bis-carbamoyl fluoride starting material. The bis-carbamoyl fluoride is then reacted with an appropriate oxime to yield compounds of Formula I.

The azo phenols and azo naphthols are well known in the art of dye chemistry. For a description of synthetic procedures see H. Zollinger, "Diazo and Azo Chemistry", Interscience Publishers, Inc., New York, 1961.

The following example further illustrates the method for synthesizing compounds of this invention. All parts and percentages are by weight and all temperatures are in degrees centigrade (°C.).

EXAMPLE 1

Methyl N-[N-[N-[4-(2,6-diethylphenylazo)-2-methylphenoxycarbonyl]-N-methylaminothio]-N-methylaminocarbonyloxy]ethanimidothioate 2.7 grams of 4-[(2,6-diethylphenyl)azo]-2-methylphenol was dissolved in 50 ml of dimethylformamide. To the solution at room temperature was added, all at once, 0.48 grams of a 50% mineral oil dispersion of sodium hydride. After the reaction to form the sodium salt of the phenol was complete, a solution of 2.7 grams of methyl N-[[(N-[(N-fluorocarbonyl-N-methylamino)thio-N-methylaminocarbonyloxy]]e- thanimidothioate in 20 ml of dimethylformamide, was added dropwise over 5 minutes to the reaction mixture. The mixture was stirred for 24 hours at room temperature and then poured into 500 ml of distilled water. The aqueous mixture of the product was extracted with 3 200 ml portions of methylene chloride. The solution of the product was dried with anhydrous sodium sulfate and then filtered. The solvent was removed at reduced pressure on a rotary evaporator. The crude product was further purified by dry column chromatography on silica gel eluting with 50% ethyl acetate/hexane. 0.55 grams of reddish oil was obtained with nmr (CDCl$_3$S) 1.2 (t, 6H), 2.3–3.1 (M, 13H), 3.7 (2S, 6H), 7.6–8.2 (6H).

Following the procedure of Example 1 with the appropriate carbamoyl fluoride (1) and phenol or naphthol (2), the following compounds may be prepared.

| R | R$_1$ | A | Physical Properties |
|---|---|---|---|
| CH$_3$\_>=N—<br>CH$_3$S/ | CH$_3$ | O—⟨phenyl⟩—N=N—⟨phenyl⟩ | nmr (δ,CDCl$_3$),<br>2.4 (2s, 6H),<br>3.6 (2s, 6H),<br>7.2–8.7 (m, 9H) |
| CH$_3$\_>=N—<br>CH$_3$S/ | CH$_3$ | O—⟨phenyl with 2-CH$_3$, 5-CH$_3$⟩—N=N—⟨phenyl⟩ | |
| CH$_3$\_>=N—<br>CH$_3$S/ | CH$_3$ | O—⟨phenyl with CH$_3$⟩—N=N—⟨phenyl⟩ | |
| CH$_3$\_>=N—<br>CH$_3$S/ | CH$_3$ | O—⟨phenyl with 2-CH$_3$, 6-CH$_3$⟩—N=N—⟨phenyl⟩ | |
| CH$_3$\_>=N—<br>CH$_3$S/ | CH$_3$ | O—⟨phenyl with CH$_2$CH$_3$⟩—N=N—⟨phenyl⟩ | |
| CH$_3$\_>=N—<br>CH$_3$S/ | CH$_3$ | O—⟨phenyl with CH$_2$CH$_2$CH$_3$⟩—N=N—⟨phenyl⟩ | |
| CH$_3$\_>=N—<br>CH$_3$S/ | CH$_3$ | O—⟨phenyl with C(CH$_3$)$_3$⟩—N=N—⟨phenyl with CH$_3$⟩ | |
| CH$_3$\_>=N—<br>CH$_3$S/ | CH$_3$ | O—⟨phenyl with CH$_3$⟩—N=N—⟨phenyl-CH$_3$⟩ | |
| CH$_3$\_>=N—<br>CH$_3$S/ | CH$_3$ | O—⟨phenyl with CH$_3$⟩—N=N—⟨phenyl with CH$_3$⟩ | |
| CH$_3$\_>=N—<br>CH$_3$S/ | CH$_3$ | O—⟨phenyl with Cl⟩—N=N—⟨phenyl⟩ | |

-continued

| R | R₁ | A | Physical Properties |
|---|---|---|---|
| CH₃(CH₃S)C=N— | CH₃ | 4-(phenylazo)-2-bromophenolate | |
| CH₃(CH₃S)C=N— | CH₃ | 4-[(4-methylphenyl)azo]-2-iodophenolate | |
| CH₃(CH₃S)C=N— | CH₃ | 2-methoxy-5-(phenylazo)benzoic acid (with —O⁻ and CO₂H) | |
| CH₃(CH₃S)C=N— | CH₃ | 4-(phenylazo)-2-sulfonatophenolate sodium salt (SO₃Na) | |
| CH₃(CH₃S)C=N— | CH₃ | 2-(phenylazo)phenolate | |
| CH₃(CH₃S)C=N— | CH₃ | 4-(phenylazo)-1-naphtholate | |
| CH₃(CH₃S)C=N— | CH₃ | 1-(phenylazo)-2-naphtholate | |

-continued

| R | $R_1$ | A | Physical Properties |
|---|---|---|---|
| $\begin{array}{c}CH_3\\CH_3S\end{array}\!\!>\!\!N\!\!-$ | $CH_3$ | naphthyl-O— with —N=N—phenyl substituent | |
| $\begin{array}{c}CH_3\\CH_3S\end{array}\!\!>\!\!N\!\!-$ | $CH_3$ | 3-SO$_3$Na, 2-NH, 4-(N=N-phenyl) naphthyl | |
| $\begin{array}{c}CH_3\\CH_3S\end{array}\!\!>\!\!N\!\!-$ | $CH_3$ | O—(3-CH$_3$-phenyl)—N=N—(2,5-diCl-phenyl) | |
| $\begin{array}{c}CH_3\\CH_3S\end{array}\!\!>\!\!N\!\!-$ | $CH_3$ | O—(3-CH$_3$-phenyl)—N=N—(4-CH$_2$CH$_3$-phenyl) | |
| $\begin{array}{c}CH_3\\CH_3S\end{array}\!\!>\!\!N\!\!-$ | $CH_3$ | O—(3-CH$_3$-phenyl)—N=N—(4-CH$_2$CH$_2$CH$_3$-phenyl) | |
| $\begin{array}{c}CH_3\\CH_3S\end{array}\!\!>\!\!N\!\!-$ | $CH_3$ | O—(3-CH$_3$-phenyl)—N=N—(4-CH(CH$_3$)$_2$-phenyl) | |
| $\begin{array}{c}CH_3\\CH_3S\end{array}\!\!>\!\!N\!\!-$ | $CH_3$ | O—(3-CH$_3$-phenyl)—N=N—(4-CH$_2$CH$_2$CH$_2$—CH$_3$-phenyl) | |
| $\begin{array}{c}CH_3\\CH_3S\end{array}\!\!>\!\!N\!\!-$ | $CH_3$ | O—(3-CH$_3$-phenyl)—N=N—(4-CH(CH$_3$)CH$_2$CH$_3$-phenyl) | |
| $\begin{array}{c}CH_3\\CH_3S\end{array}\!\!>\!\!N\!\!-$ | $CH_3$ | O—(3-CH$_3$-phenyl)—N=N—(4-C(CH$_3$)$_3$-phenyl) | |

-continued

| R | $R_1$ | A | Physical Properties |
|---|---|---|---|
| $(CH_3)(CH_3S)C=N-$ | $CH_3$ | 4-hydroxy-3-methylphenyl azo 2-bromophenyl | |
| $(CH_3)(CH_3S)C=N-$ | $CH_3$ | 4-hydroxy-3-methylphenyl azo 3-nitrophenyl | |
| $(CH_3)(CH_3S)C=N-$ | $CH_3$ | 4-hydroxy-3-methylphenyl azo 2-carboxyphenyl | |
| $(CH_3)(CH_3S)C=N-$ | $CH_3$ | 4-hydroxy-3-methylphenyl azo 2-methoxyphenyl | |
| $(CH_3)(CH_3S)C=N-$ | $CH_3$ | 4-hydroxy-3-methylphenyl azo 4-ethoxyphenyl | |
| $(CH_3)(CH_3S)C=N-$ | $CH_3$ | 4-hydroxy-3-methylphenyl azo 4-propoxyphenyl | |
| $(CH_3)(CH_3S)C=N-$ | $CH_3$ | 4-hydroxy-3-methylphenyl azo 4-isopropoxyphenyl | |
| $(CH_3)(CH_3S)C=N-$ | $CH_3$ | 4-hydroxy-3-methylphenyl azo (2-sulfonato-sodium naphthyl) | |
| $(CH_3)(CH_3S)C=N-$ | $CH_3$ | 4-hydroxy-3-methylphenyl azo (6-sulfonato-sodium naphthyl) | |
| $(CH_3)(CH_3S)C=N-$ | $CH_3$ | 4-hydroxy-3-methylphenyl azo naphthyl | |

4,216,147

-continued

| R | R₁ | A | Physical Properties |
|---|---|---|---|
| 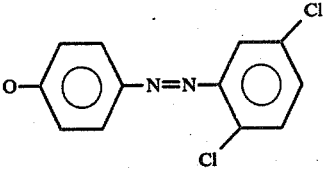 CH₃, CH₃S >C=N— | CH₂CH₃ | 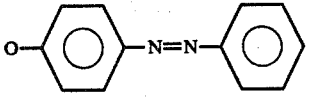 O—⟨phenyl⟩—N=N—⟨phenyl, 2-Cl, 5-Cl⟩ | |
| CH₃, CH₃S >C=N— | —CH₂CH₂CH₃ | O—⟨phenyl⟩—N=N—⟨phenyl⟩ | |
| CH₃, CH₃S >C=N— | —CH(CH₃)₂ | O—⟨phenyl⟩—N=N—⟨phenyl⟩ | |
| CH₃, CH₃CH₂S >C=N— | —CH₃ | O—⟨phenyl⟩—N=N—⟨phenyl⟩ | |
| CH₃, CH₃CH₂CH₂S >C=N— | CH₃ | O—⟨3-CH₃-phenyl⟩—N=N—⟨2,6-(CH₂CH₃)₂-phenyl⟩ | |
| CH₃, (CH₃)₂CHS >C=N— | CH₃ | O—⟨3-CH₃-phenyl⟩—N=N—⟨2,6-(CH₂CH₃)₂-phenyl⟩ | |
| CH₃CH₂, CH₃S >C=N— | CH₃ | O—⟨3-CH₃-phenyl⟩—N=N—⟨2,6-(CH₂CH₃)₂-phenyl⟩ | |
| CH₃CH₂CH₂, CH₃S >C=N— | CH₃ | O—⟨3-CH₃-phenyl⟩—N=N—⟨2,6-(CH₂CH₃)₂-phenyl⟩ | |
| (CH₃)₂CH, CH₃S >C=N— | CH₃ | O—⟨3-CH₃-phenyl⟩—N=N—⟨2,6-(CH₂CH₃)₂-phenyl⟩ | |
| CH₃OCH₂, CH₃S >C=N— | CH₃ | O—⟨3-CH₃-phenyl⟩—N=N—⟨2,6-(CH₂CH₃)₂-phenyl⟩ | |
| (CH₃)₂N—C(=O)—C(SCH₃)=N— | CH₃ | O—⟨3-CH₃-phenyl⟩—N=N—⟨2,6-(CH₂CH₃)₂-phenyl⟩ | |

-continued

| R | R₁ | A | Physical Properties |
|---|---|---|---|
| CH₃S-C(CH₃)(CH₃)-CH=N- (with H) | CH₃ | 2-methyl-4-[(2,6-diethylphenyl)azo]phenoxy (O-phenyl with CH₃, N=N, phenyl with 2× CH₂CH₃) | |
| (CH₃)(CH₃S)C=N- | CH₃ | 2-methyl-5-chloro-4-(phenylazo)phenoxy | |
| (CH₃)(CH₃S)C=N- | CH₃ | 2-bromo-5-chloro-4-(phenylazo)phenoxy (with Cl, Br substituents) | |
| (CH₃)(CH₃S)C=N- | CH₃ | 2-iodo-5-chloro-4-(phenylazo)phenoxy (with Cl, I substituents) | |
| (CH₃)(CH₃S)C=N- | CH₃ | 4-methyl-3-(phenylazo)-6-carboxyphenoxy (O-phenyl with CH₃, CO₂H, N=N-phenyl) | |
| (CH₃)(CH₃S)C=N- | CH₃ | 4-methyl-3-(phenylazo)-6-sulfonatophenoxy (O-phenyl with CH₃, SO₃Na, N=N-phenyl) | |
| (CH₃)(CH₃S)C=N- | CH₃ | 2,5-disubstituted (CH₃, CH₂CH₃) -4-(phenylazo)phenoxy | |
| (CH₃)(CH₃S)C=N- | CH₃ | 2-methyl-5-propyl-4-(phenylazo)phenoxy (O-phenyl with CH₃, CH₂CH₂CH₃, N=N-phenyl) | |
| (CH₃)(CH₃S)C=N- | CH₃ | 2-methyl-5-isopropyl-4-(phenylazo)phenoxy (O-phenyl with CH₃, CH(CH₃)CH₃, N=N-phenyl) | |
| (CH₃)(CH₃S)C=N- | CH₃ | 2-methyl-5-tert-butyl-4-(phenylazo)phenoxy (O-phenyl with CH₃, C(CH₃)₂CH₃, N=N-phenyl) | |

-continued

| R | R₁ | A | Physical Properties |
|---|----|---|---------------------|
| $\begin{array}{c}CH_3\\CH_3S\end{array}\!\!>\!=\!N-$ | CH₃ | 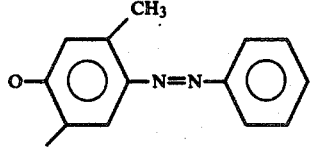 | |
| $\begin{array}{c}CH_3\\CH_3S\end{array}\!\!>\!=\!N-$ | CH₃ | 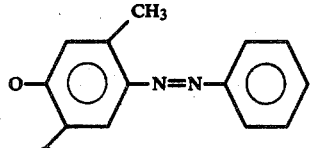 | |

Formulation

Useful formulations of the compounds of Formula I can be prepared in conventional forms. They include dusts, granules, pellets, solutions, emulsions, emulsifiable concentrates and the like. Many of these may be applied directly. Sprayable formulations can be extended in suitable media and used at spray volumes of from a few pints to several hundred gallons per acre. High strength compositions are primarily used as intermediates for further formulations. The formulations, broadly, contain about 1% to 99% by weight of active ingredient(s) and at least one of (a) about 0.1% to 20% surfactant(s) and (b) about 1% to 99% solid or liquid diluent(s). Preferably, formulations of the compounds of this invention contain these ingredients in the following proportions:

|  | Active ingredient | Diluent(s) | Surfactant(s) |
|---|---|---|---|
| Oil Suspensions, Emulsions, Solutions (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. For example, many of the compounds are oils or relatively low melting solids. In these cases, the strength of granules must be limited because of physical handling considerations. Higher ratios of surfactant to active ingredient are sometimes desirable, and are achieved by incorporation into the formulation or by tank mixing.

Typical solid diluents are described in Watkins, et al., "Handbook of Insecticide Dust Diluents, and Carriers", 2nd Edn., Dorland Books, Caldwell, N.J. The denser diluents are preferred for dusts. Typical diluents and solvents are described in Marsden, "Solvents Guide", 2nd, Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making the compositions of this invention are generally known in the art. Solutions can be prepared by simply mixing the ingredients. Fine solid compositions can be made by blending and, usually grinding as in a hammer or fluid energy mill. Suspensions can be prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

The following examples further illustrate compositions of this invention.

EXAMPLE 2

| Solution | |
|---|---|
| Methyl N-[N-[N-[4-(2,6-diethylphenylazo)-2-methylphenoxycarbonyl]-N-methylaminothio]-N-methylaminocarbonyloxy]-ethanimidothioate | 30% |
| Dimethylformamide | 70% |

The ingredients are combined and stirred to produce a solution suitable for low volume applications.

EXAMPLE 3

| Dust | |
|---|---|
| Solution of Example A | 5% |
| Pyrophyllite (powder) | 95% |

The solution is sprayed onto the pyrophyllite diluent; the mixture is thoroughly blended and then packaged. The product is suitable for use as a dust.

EXAMPLE 4

| Emulsifiable Concentrate | |
|---|---|
| Methyl N-[N-[N-[4-(2,6-diethylphenylazo)-2-methylphenoxycarbonyl]-N-methylaminothio]-N-methylaminocarbonyloxy]-ethanimidothioate | 30% |

-continued

| Emulsifiable Concentrate | |
|---|---|
| Blend of oil soluble sulfonates | 4% |
| Xylene | 66% |

The ingredients are combined and stirred with gentle warming to speed solution. A fine screen filter is included in the packaging operation to insure the absence of any extraneous undissolved material in the product.

EXAMPLE 5

| Granule | |
|---|---|
| Solution of Example A | 15% |
| Attapulgite granules (U.S.S.# 20–40; 0.84–0.42 mm) | 85% |

The solution was sprayed on the surface of the granules in a double-cone blender. The granules were then dried and packaged.

EXAMPLE 6

| Extruded Pellet | |
|---|---|
| Methyl N-[N-[N-[4-(2,6-diethylphenylazo)-2-methylphenoxycarbonyl]-N-methylaminothio]-N-methylaminocarbonyloxy]-ethanimidothioate | 15% |
| Anhydrous sodium sulfate | 10% |
| Crude calcium ligninsulfonate | 5% |
| Sodium alkylnaphthalenesulfonate | 1% |
| Calcium/magnesium bentonite | 69% |

The ingredients were blended, hammer milled and then moistened with about 12% water. The mixture was extruded as cylinders about 3 mm diameter which are cut to produce pellets about 3 mm long. These may be used directly after drying, or the dried pellets may be crushed to pass a U.S.S. No. 20 sieve (0.84 mm opening). The granules held on a U.S.S. No. 40 sieve (0.42 mm opening) may be packaged for use and the fines recycled.

Utility

The compounds of this invention are useful for control of insects and nematodes which are detrimental to agriculture.

The compounds of this invention readily control pestiferous insects belonging to such orders as Lepidoptera and Coleoptera. More specifically, insects controlled by the compounds of this invention include southern armyworm (*Spodoptera eridania*), fall armyworm (*Spodoptera frugiperda*), soybean looper (*Pseudoplusia includens*), Mexican bean beetle (*Epilachna varivestis*), tobacco budworm (*Heliothis virescens*) and bollworm (*Heliothis zea*).

The compounds of this invention also control pestiferous nematodes, such as the root-knot nematode, *Meloidogyne incognita;* lesion nematode, Pratylenchus spp. and dagger nematode, Xiphinima.

Insects are normally controlled by applying one or more of the compounds to the locus of infestation, to the area to be protected, or to the pests themselves. For the control of insects on agricultural crops, compounds of this invention are generally applied to the foliage or other plant parts which are infested or which are to be protected. Effective amounts to be applied depend upon the specific compound used, the species to be controlled, its life stage, its size and location, the amount of rainfall, the time of year, moisture, temperature, type of application, plant spacing, and other variables. In general, 0.05 to 10 Kg/ha may be required for insect control in agriculture with rates of 0.15 to 5 Kg/ha usually being sufficient in many situations. In large scale field operations, rates in the range of 0.25 to 3 Kg/ha are generally used.

Nematodes are controlled by applying the compounds to the locus of infestation, to the area to be protected or to the pest themselves. For the control of nematodes in agricultural crops, a compound of this invention is generally applied to a portion of the plant or surrounding soil which is infested or which is to be protected. Effective amounts to be applied depend upon the species to be controlled, its life stage, its size and location, the amount of rainfall, the time of year, moisture, temperature, soil type, percentage of area treated, type of application, and other variables. In general, 3 to 30 Kg/ha may be required for nematode control in agriculture with rates of 5 to 10 Kg/ha usually being sufficient in many situations.

The compounds of this invention exhibit improved residual insecticidal activity which can reduce the need for closely spaced multiple sprays. This results in greater economy to the grower and dissemination of less insecticide in the environment. An additional advantage is the reduced side-effects on cotton. Treated leaves tend to remain green and free of reddening.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate (carbendazim)
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyimino acetamide Curzate ®
N-trichloromethylthiotetrahydrophthalimide (captan)
N-trichloromethylthiophthalimide (folpet)

Bactericides tribasic copper sulfate
streptomycin sulfate

Acaricides senecioic acid, ester with 2-sec-butyl-4,6-dinitrophenol ("Morocide")
6-methyl-1,3-dithiolo[2,3-B]quinonolin-2-one ("Morestan")
ethyl 4,4'(p-chlorophenyl)-2,2,2-trichloroethanol (Kelthane ®)
bis(pentochloro-2,4-cyclopentadien-lyl) (Pentac ®)
tricyclohexyltin hydroxide (Plictran ®)

Nematicides

2-[diethoxyphosphinylimino]-1,3-dithietane (Nematak®)

S-methyl 1-(dimethylcarbamoyl)-N-(methylcarbamoyloxy)-thioformimidate

S-methyl 1-carbamoyl-N-(methylcarbamoyloxy)thioformidate

N-isopropylphosphoramidic acid, O-ethyl-O'[4-(methylthio)-m-tolyl]diester ("Nemacur")

Insecticides 3-hydroxy-N-methylcrotonamide(dimethylphosphate)ester (Azodrin®)

methylcarbamic acid, ester with 2,3-dihydro-2,2-dimethyl-7-benzofuranol (Furadan®)

O-[2,4,5-trichloro-α-(chloromethyl)benzyl]phosphoric acid, O',O'-dimethyl ester (Gardona®)

2-mercaptosuccinic acid, diethyl ester, S-ester with thionophosphoric acid, dimethyl ester (Malathion®)

phosphorothioic acid, O,O-dimethyl, O-p-nitrophenyl ester (methyl parathion)

methylcarbamic acid, ester with α-naphthol (Sevin®)

methyl N-[[(methylamino)carbonyl]oxy]ethanimidothioate (methomyl)

N'-(4-chloro-o-tolyl)-N,N-dimethylformamidine (Galecron®)

O,O-diethyl-O-(2-isopropyl-4-methyl-6-pyrimidylphosphorothioate (Diazinon®)

octachlorocamphene (toxaphene)

O-ethyl O-p-nitrophenyl phenylphosphonothioate (EPN)

cyano(3-phenoxyphenyl)-methyl-4-chloro-α-(1-methylethyl)-benzeneacetate (Pydrin®)

(3-phenoxyphenyl)methyl(±)-cis,trans-3-(2,2-dichloroethenyl)-2,2-dimethylcyclopropanecarboxylate (Ambush®)

dimethyl N,N'-[thiobis[(N-methylimino)carbonyloxy]]-bis[ethanimidothioate] (Larvin®)

O-ethyl-S-(p-chlorophenyl)ethylphosphonodithioate (Curacron®)

phosphorothiolothionic acid, O-ethyl-O-[4-(methylthio)-phenyl]-S-n-propyl ester (Bolstar®)

EXAMPLE 7

The foliage only of red kidney bean plants in the two-leaf stage was sprayed to run-off with dispersions of compounds of this invention at various concentrations. Dispersions were prepared by dissolving appropriately weighed quantities of the active ingredient in 10 ml of acetone and diluting to 100 ml of water containing a surface active agent (Duponol® L-144 WDG) at 1:3000. After drying, leaves were excised and placed in covered 10 cm petri dishes along with moist filter paper to keep them fresh. Ten southern armyworm larvae were placed in each dish. Tests were run in duplicate. The units were kept in a room maintained at 25°±2° C., 53±5% RH. Results were recorded at the end of 2 days.

| Compound | % Concentration | % Mortality |
| --- | --- | --- |
| Methyl N-[N-[N-[4-(2,6-dimethylphenylazo)-2-methylphenoxycarbonyl]-N-methylaminothio]-N-methylaminocarbonyloxy]-ethanimidothioate | .01 | 95 |
|  | .005 | 90 |
| Methyl N-[N-methyl-N- | .01 | 95 |

| Compound | % Concentration | % Mortality |
| --- | --- | --- |
| [N-methyl-N-[4-(phenylazo)-phenoxycarbonyl]aminothio]-aminocarbonyloxy]-ethanimidothioate | .005 | 70 |
| Untreated | — | 0 |

EXAMPLE 8

The foliage of red kidney bean plants in the two-leaf stage was sprayed to run-off with dispersions of compounds of this invention at various concentrations. Dispersions were prepared by dissolving appropriately weighed quantities of the active ingredient in 10 ml of acetone and diluting to 100 ml with water containing a surface active agent (Duponol® L-144 WDG) at 1:3000. After drying, plants were placed under artificial light in a room maintained at 25°±2° C., 54±5% RH. After the designated period, leaves were excised and placed in covered 10 cm petri dishes along with moist filter paper to keep them fresh. Ten southern armyworm larvae were placed in each dish. Tests were run in duplicate. The units kept in a room maintained at 25°±2° C., 54±5% RH. Results were recorded at the end of 7 days.

| Compound | % Concentration | % Mortality |
| --- | --- | --- |
| Methyl-N-[N-[N-[4-(2,6-dimethylphenylazo)-2-methylphenoxycarbonyl]-N-methylaminothio]-N-methylaminocarbonyloxy]-ethanimidothioate | .01 | 100 |
|  | .005 | 95 |
| Methyl N-[[(methylamino)carbonyl]oxy]ethanimidothioate (methomyl) | .01 | 0 |
|  | .005 | 0 |
| Untreated | — | 0 |

EXAMPLE 9

Potted cotton plants approximately 25 cm high having 3–4 true leaves were sprayed to run-off with aqueous dispersions of compounds of this invention at 500 ppm. The sprays contained a surface active agent (Duponol® L-144 WDG) at a concentration of 1:3000. Another set of plants was similarly treated with methomyl. After drying, the plants were set out in the greenhouse and held for observation. Results were recorded after 5 days.

| Compound (500 ppm AI)[1] | Rating[2] (5 days) |
| --- | --- |
| Methyl N-[N-[N-[4-(2,6-dimethylphenylazo)-2-methylphenoxycarbonyl]-N-methylaminothio]-N-methylaminocarbonyloxy]-ethanimidothioate | 0 |
| Methyl N-[[(methylamino)carbonyl]oxy]-ethanimidothioate (methomyl) | 3R |
| Untreated control | 0 |

[1] AI - active ingredient
[2] "R" denotes typical methomyl effect, i.e., reddening of older leaves, slight puckering and black stippling of younger leaves. Rating is on the basis of 0 to 10 with 0 indicating no effect and 10 indicating total leaf area involvement.

EXAMPLE 10

Tobacco budworm (*Heliothis virescens*) larvae were treated topically with compounds of this invention. One microliter of each concentration used was applied to the dorso-thoracic area of each larva tested. The stock solutions were prepared by dissolving appropriately weighed quantities of active ingredient in predetermined quantities of acetone. Further diluting with acetone yielded the desired concentrations. Larvae were treated in individual 1-oz. cups in which they were reared on artificial diet. Twelve larvae were treated with each desired concentration and kept in a room at 25°±2° C. Results were recorded 2 days after treatment.

| Compound | Concentration (μg/larva) | % Mortality (48 hours) |
|---|---|---|
| Methyl N-[N-[N-[4-(2,6-dimethylphenylazo)-2-methylphenoxycarbonyl]-N-methylaminothio]-N-methylaminocarbonyloxy]-ethanimidothioate | 0.5 | 92 |
|  | 0.25 | 83 |
| Methyl parathion | 10 | 50 |
| Untreated | — | 0 |

EXAMPLE 11

Methyl N-[N-[N-[4-(2,6-dimethylphenylazo)-2-methylphenoxycarbonyl]-N-methylaminothio]-N-methylaminocarbonyloxy]-ethanimidothioate was dissolved in acetone and mixed into soil containing the root-knot nematode, *Meloidogyne incognita*. Dimethyl N,N',[[1,3-propanediylbis[oxycarbonyl(N-methylimino)thio-(N-methylimino)carbonyloxy]]]bis-[ethanimidothioate], was similarly dissolved in acetone and mixed into soil containing the root-knot nematode, *Meloidogyne incognita*. The treated soil samples were planted with cucumber seeds. After 2 weeks, the roots were examined for nematode injury and the results are summarized below.

| Compound | kg/ha | % Nematode Control |
|---|---|---|
| Methyl N-[N-[N-[4-(2,6-dimethylphenylazo)-2-methylphenoxycarbonyl]-N-methylaminothio]-N-methylaminocarbonyloxy]-ethanimidothioate | 15 | 100 |
| Untreated control |  | 0 |

The phrase "consisting essentially of" is intended to have its customary meaning: namely, that all specified materials and conditions are very important in practicing the invention but that unspecified materials and conditions are not excluded as long as they do not prevent the benefits of the invention from being realized.

What is claimed is:

1. A compound of the formula

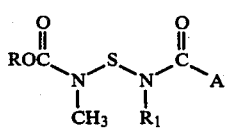

wherein

R is

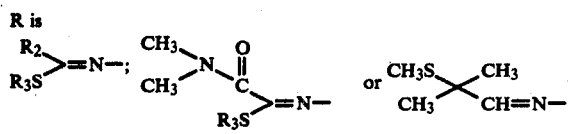

where
$R_1$ and $R_3$ are $C_1$–$C_3$ alkyl;
$R_2$ is $C_1$–$C_3$ alkyl or $CH_3OCH_2$; and

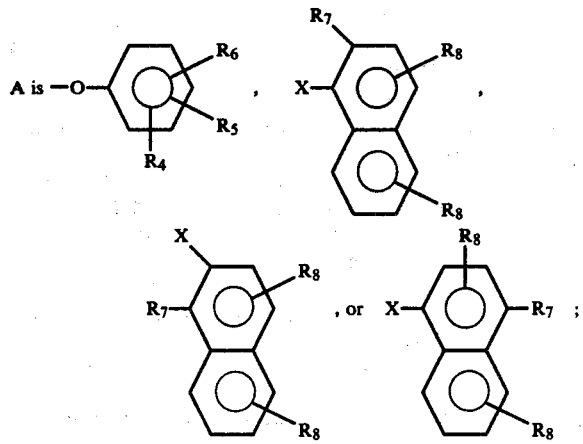

where
$R_4$ and $R_5$ are H, $C_1$–$C_4$ alkyl, halogen, —$CO_2H$ or —$SO_3Na$;
$R_6$ is o or p —N=N—B;
$R_7$ is —N=N—B;
$R_8$ is H or $SO_3Na$;

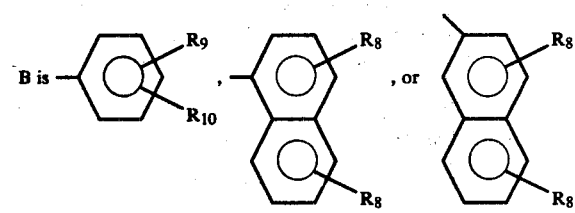

where
$R_9$ and $R_{10}$ are H, $C_1$–$C_4$ alkyl, halogen, —$CO_2H$, —$SO_3Na$, $NO_2$, or $C_1$–$C_3$ alkoxy; and
X is NH or O.

2. The compound of claim 1 wherein X is oxygen.

3. The compound of claim 1 wherein

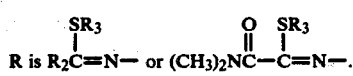

4. The compound of claim 1 wherein

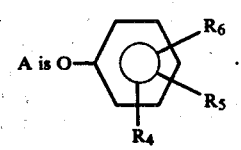

5. The compound of claim 2 wherein

6. The compound of claim 1 wherein

A is 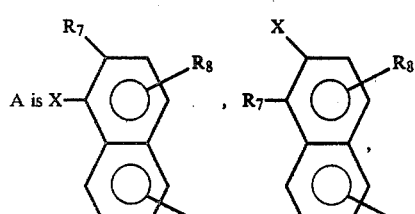, 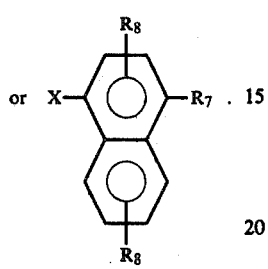

or 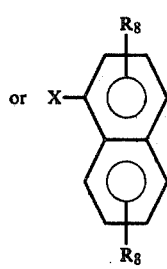

7. The compound of claim 1 wherein

B is 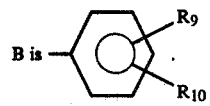

R is $R_2C=N-$ 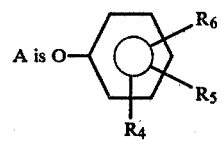 or $(CH_3)_2NC(=O)-C(SR_3)=N-$ and

A is O— 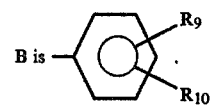

8. The compound of claim 7 wherein

B is (with $R_9$, $R_{10}$)

9. The compound of claim 8 wherein

R is $R_2C=N-$ with $SR_3$, $R_2$ is $C_1-C_2$ alkyl and $R_3$ is methyl.

10. The compound of claim 1 which is methyl N-[N-[N-[4-(2,6-dimethylphenylazo)-2-methylphenoxycarbonyl]-N-methylaminothio]-N-methylaminocarbonyloxy]ethanimidothioate.

* * * * *